United States Patent [19]

Fuchs et al.

[11] 4,199,596
[45] Apr. 22, 1980

[54] COMBATING ARTHROPODS WITH FLUORINE-SUBSTITUTED PHENOXYBENZYLCARBONYL DERIVATIVES

[75] Inventors: Rainer Fuchs, Wuppertal; Ingeborg Hammann, Cologne; Wolfgang Behrenz, Overath; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 932,597

[22] Filed: Aug. 10, 1978

[30] Foreign Application Priority Data

Sep. 3, 1977 [DE] Fed. Rep. of Germany ....... 2739854

[51] Int. Cl.² .................. A01N 9/20; A01N 9/24; C07C 69/74; C07C 121/75
[52] U.S. Cl. .................. 424/304; 260/340.5 R; 260/465 D; 260/465 F; 260/600 R; 424/282; 424/305; 424/306; 424/308; 560/9; 560/20; 560/73; 560/105; 560/124; 568/637; 568/639
[58] Field of Search .................. 260/465 D; 560/124, 560/105; 424/304, 305, 308, 306

[56] References Cited

U.S. PATENT DOCUMENTS

| | | | |
|---|---|---|---|
| 3,666,789 | 5/1972 | Itaya et al. | 424/305 |
| 3,835,176 | 9/1974 | Matsuo et al. | 260/465 D |
| 3,973,036 | 8/1976 | Hirano et al. | 560/124 |
| 3,996,244 | 12/1976 | Fujimoto et al. | 260/332.2 A |

*Primary Examiner*—Dolph H. Torrence
*Attorney, Agent, or Firm*—Sprung, Felfe, Horn, Lynch & Kramer

[57] ABSTRACT

Fluorine substituted phenoxybenzylcarbonyl derivatives of the formula

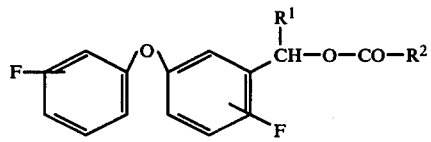

in which
$R^1$ represents hydrogen, cyano or ethynyl and
$R^2$ represents the radical

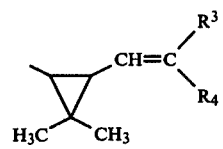

wherein
$R^3$ and $R^4$, which are identical, each represent chlorine, bromine or methyl, or
$R^2$ represents the radical

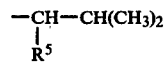

wherein
$R^5$ represents a phenyl ring which optionally carries one or more substituents each selected independently from halogen, alkyl, alkylthio and alkoxy each with 1–4 carbon atoms, nitro and methylenedioxy,
which possess arthropodicidal properties. The benzyl alcohol components of these esters are also new.

9 Claims, No Drawings

COMBATING ARTHROPODS WITH FLUORINE-SUBSTITUTED PHENOXYBENZYLCARBONYL DERIVATIVES

The present invention relates to and has for its object the provision of particular new fluorine-substituted phenoxybenzylcarbonyl derivatives which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It has already been disclosed that certain phenoxybenzyl acetates or carboxylates, for example 3'-phenoxybenzyl α-isopropyl-(3,4-dimethoxyphenyl)-acetate and 3'-[2-fluoro- or 4-fluorophenoxy]-α-cyanobenzyl [2,2-dimethyl-3-(2,2-dichlorovinyl)-cyclopropane]-carboxylate, possess insecticidal and acaricidal properties (see German Offenlegungsschriften (German Published Specifications) Nos. 2,335,347 and 2,547,534 and Belgian Pat. Specification No. 801,946).

The present invention now provides, as new compounds, the fluorine-substituted phenoxybenzyloxycarbonyl derivatives of the general formula

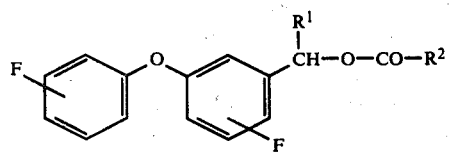

in which
R$^1$ represents hydrogen, cyano or ethynyl and
R$^2$ represents the radical

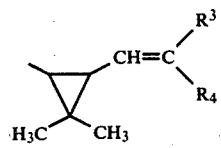

wherein
R$^3$ and R$^4$, which are identical, each represent chlorine, bromine or methyl, or
R$^2$ represents the radical

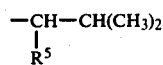

wherein
R$^5$ represents a phenyl ring which optionally carries one or more substituents each selected independently from halogen, alkyl, alkylthio and alkoxy each with 1–4 carbon atoms, nitro and methylenedioxy.

The general formula (I) embraces the various possible stereoisomers, the optical isomers and mixtures of these components.

Preferably, R$^1$ represents hydrogen or cyano and R$^2$ represents the 2,2-dimethyl-3-(2,2-dichloro-, 2,2-dibromo- or 2,2-dimethyl-vinyl)-cyclopropane radical or the α-isopropylbenzyl radical which optionally carries one or more substituents in the ring selected independently from fluorine, chlorine, bromine and straight-chain or branched alkyl with 1 to 3 carbon atoms.

Surprisingly, the fluorine-substituted phenoxybenzyloxycarbonyl derivatives of the present invention exhibit a better insecticidal and acaricidal action than the corresponding previously known products of analogous structure and of the same type of action. The products according to the present invention thus represent a genuine enrichment of the art.

The present invention also provides a process for the preparation of a fluorine-substituted phenoxybenzyloxycarbonyl derivative of the formula (I) in which (a) a carbonyl halide of the general formula

in which
R$^2$ has the above-mentioned meaning and
Hal represents halogen, preferably chlorine, is reacted with a fluorine-substituted phenoxybenzyl alcohol of the general formula

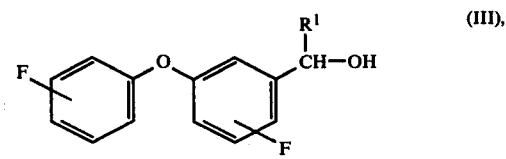

in which
R$^1$ has the above-mentioned meaning, if appropriate in the presence of an acid acceptor and, if appropriate, in the presence of a diluent or solvent, or (b) a carboxyl derivative of the general formula

in which
R$^2$ has the above-mentioned meaning, is reacted, as such in the presence of an acid acceptor or in the form of an alkali metal salt, alkaline earth metal salt or ammonium salt, with a fluorine-substituted phenoxybenzyl halide of the general formula

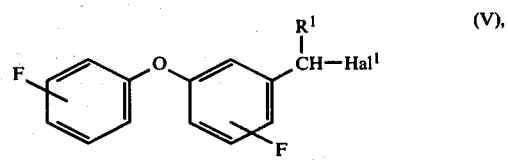

in which
R$^1$ has the stated meaning and
Hal$^1$ represents halogen, preferably bromine, if appropriate in the presence of a diluent or solvent.

If, for example, 2-fluoro-5-(3-fluorophenoxy)-α-cyanobenzyl alcohol or bromide and α-isopropyl-4-ethylphenylacetic acid chloride or sodium α-isopropyl-4-ethylphenylacetate are used as the starting materials, the source of the reaction in process variants (a) and (b) can be represented by the following equations:

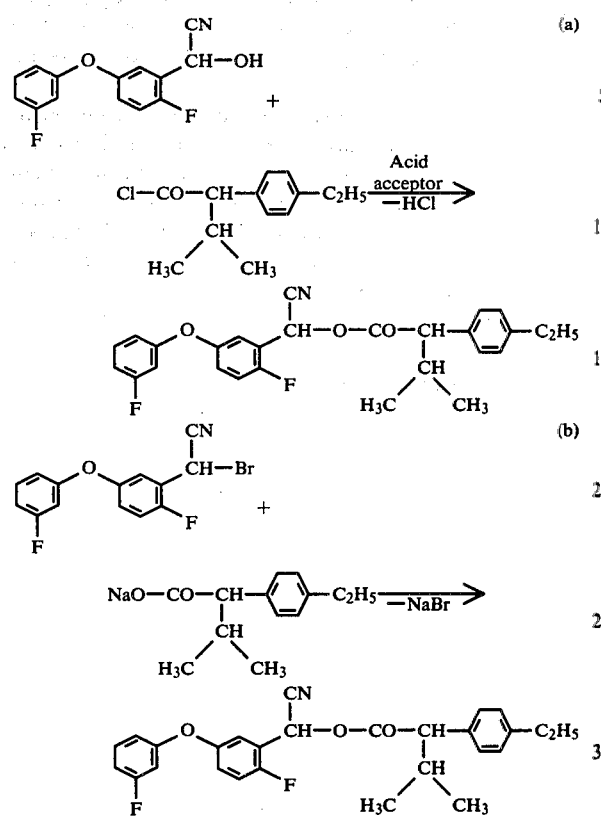

Carbonyl halides (II) and carboxyl derivatives (IV) to be used as starting materials are known and can be prepared in accordance with generally customary processes described in the literature (see, for example, German Offenlegungsschrift (German Published Specification Nos.) 2,365,555, 1,926,433 and 2,231,312).

The following may be mentioned as specific examples thereof: 2,2-dimethyl-3-(2,2-dichlorovinyl)-cyclopropanecarboxylic acid chloride, 2,2-dimethyl-3-(2,2-dibromovinyl)-cyclopropanecarboxylic acid chloride, 2,2-dimethyl-3-(2,2-dimethylvinyl)-cyclopropanecarboxylic acid chloride, α-isopropyl-phenylacetic acid chloride, α-isopropyl-4-fluorophenylacetic acid chloride, α-isopropyl-4-chlorophenyl-acetic acid chloride, α-isopropyl-4-bromophenylacetic acid chloride, α-isopropyl-4-methylphenylacetic acid chloride, α-isopropyl-4-ethylphenylacetic acid chloride, α-isopropyl-4-n-propylphenylacetic acid chloride, α-isopropyl-4-isopropylphenylacetic acid chloride, α-isopropyl-3-fluorophenylacetic acid chloride, α-isopropyl-3-bromophenylacetic acid chloride, α-isopropyl-3-chlorophenylacetic acid chloride, α-isopropyl-3-methylphenylacetic acid chloride, α-isopropyl-3-ethylphenylacetic acid chloride, α-isopropyl-3-n-propylphenylacetic acid chloride, α-isopropyl-3-isopropylphenylacetic acid chloride and the corresponding free acids.

The phenoxybenzyl alcohols (III) and phenoxybenzyl halides (V) also to be used as starting compounds have not hitherto been described in the literature, but can be obtained in a manner which is in itself known by converting the corresponding phenoxytoluenes by means of halogenating agents, for example N-bromosuccinimide, into the phenoxybenzyl halides (V) and reacting these with hexamethylenetetramine to give the corresponding phenoxybenzaldehyes of the general formula

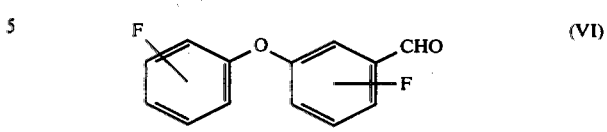

and (a¹) where $R^1$ represents hydrogen, reducing these with a complex metal hydride in an inert solvent, (b¹) where $R^1$ represents cyano, reacting these with an alkali metal cyanide, for example sodium cyanide or potassium cyanide, in the presence of an acid, with or without addition of a solvent, or (c¹) where $R^1$ represents ethynyl, reacting these with an ethynyl compound of the formula

in which

Hal represents halogen, in a suitable solvent.

If, for example, using process variant (a¹), 5-(3-fluorophenoxy)-2-fluoro-benzaldehyde and lithium aluminum hydride are used as starting materials, using process variant (b¹) 5-(3-fluorophenoxy)-2-fluoro-benzaldehyde and potassium cyanide are used as starting materials and using process variant (c¹) 5-(3-fluorophenoxy)-2-fluorobenzaldehyde and ethynyl-magnesium bromide are used as starting materials, the course of the reactions can be represented by the following equations:

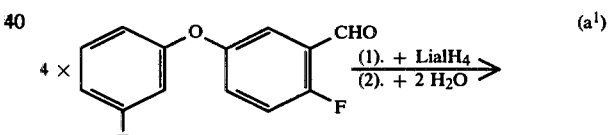

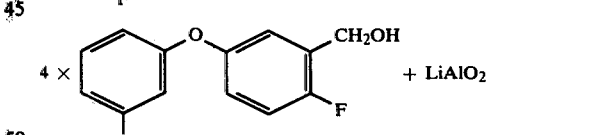

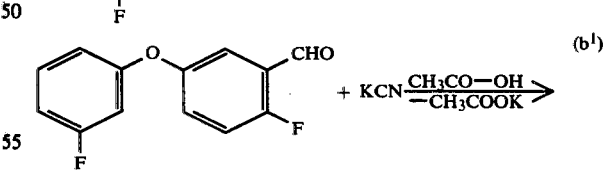

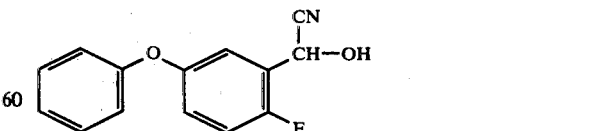

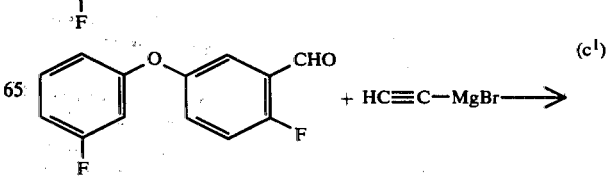

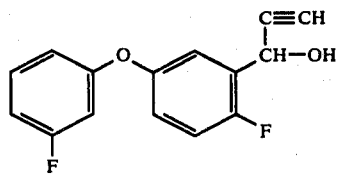

The following may be mentioned as specific examples of the fluorine-substituted phenoxybenzyl alcohols (III) and phenoxybenzyl bromides (V) to be used as starting materials: 2-fluoro-3-(2-fluorophenoxy)-benzyl alcohol, 4-fluoro-3-(2-fluorophenoxy)-benzyl alcohol, 5-fluoro-3-(2-fluorophenoxy)-benzyl alcohol, 6-fluoro-3-(2-fluorophenoxy)-benzyl alcohol, 2-fluoro-3-(3-fluorophenoxy)-benzyl alcohol, 4-fluoro-3-(3-fluorophenoxy)-benzyl alcohol, 5-fluoro-3-(3-fluorophenoxy)-benzyl alcohol, 6-fluoro-3-(3-fluorophenoxy)-benzyl alcohol, 2-fluoro-3-(4-fluorophenoxy)-benzyl alcohol, 4-fluoro-3-(4-fluorophenoxy)-benzyl alcohol, 5-fluoro-3-(4-fluorophenoxy)-benzyl alcohol, 6-fluoro-3-(4-fluorophenoxy)-benzyl alcohol, 2-fluoro-3-(2-fluorophenoxy)-α-cyanobenzyl alcohol, 4-fluoro-3-(2-fluorophenoxy)-α-cyanobenzyl alcohol, 5-fluoro-3-(2-fluorophenoxy)-α-cyanobenzyl alcohol, 6-fluoro-3-(2-fluorophenoxy)-α-cyanobenzyl alcohol, 2-fluoro-3-(3-fluorophenoxy)-α-cyanobenzyl alcohol, 4-fluoro-3-(3-fluorophenoxy)-α-cyanobenzyl alcohol, 5-fluoro-3-(3-fluorophenoxy)-α-cyanobenzyl alcohol, 6-fluoro-3-(3-fluorophenoxy)-α-cyanobenzyl alcohol, 2-fluoro-3-(4-fluorophenoxy)-α-cyanobenzyl alcohol, 4-fluoro-3-(4-fluorophenoxy)-α-cyanobenzyl alcohol, 5-fluoro-3-(4-fluorophenoxy)-α-cyanobenzyl alcohol, 6-fluoro-3-(4-fluorophenoxy)-α-cyanobenzyl alcohol and the corresponding -benzyl bromides.

All customary acid-binding agents can be used as acid acceptors for the preparation of the fluorine-substituted phenoxybenzyloxycarbonyl derivatives according to the invention. Alkali metal carbonates and alkali metal alcoholates, such as sodium carbonate and potassium carbonate, sodium methylate and ethylate and potassium methylate and ethylate, have proved particularly successful, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at from 0° to 150° C., preferably at from 15° to 40° C. in the case of process variant (a) and at from 100° to 130° C. in the case of process variant (b).

The reaction is in general allowed to take place under normal pressure.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane ketones, for example acetone, methyl ethyl ketone, methyl isopropyl ketone and methyl isobutyl ketone; nitriles, such as acetonitrile and propionitrile; and dimethylformamide.

To carry out process variant (a), the starting compounds are preferably employed in equimolar ratios. An excess of one or other reactant produces no significant advantages. In general, the reactants are brought together in one of the stated solvents and are stirred for one or more hours, in most cases at an elevated temperature, in order to complete the reaction. The reaction mixture is then poured into water and the organic phase is separated off and subsequently washed with water. After drying, the solvent is distilled off in vacuo.

In process variant (b), the carboxyl derivative component is preferably employed in the form of a salt (for example the sodium salt) in a solvent and the phenoxybenzyl halide is added in 10-20% excess. After heating for several hours, the solvent is distilled off, the residue is taken up in an organic solvent, the organic phase is washed and dried and the residue is distilled off.

The new compounds are obtained in the form of oils which in a number of cases cannot be distilled without decomposition but are freed from the last volatile constituents by so-called "incipient distillation", that is to say by prolonged heating under reduced pressure to moderately elevated temperatures, and are purified in this manner. They are characterized by the refractive index.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the *Isopoda*, for example *Oniscus asellus, Armadillidium vulgare* and *Porcellio scaber;* from the class of the *Diplopoda*, for example *Blaniulus guttulatus;* from the class of the *Chilopoda*, for example *Geophilus carpophagus* and *Scutigera* spec.;

from the class of the *Symphyla*, for example *Scutigerella immaculata;* from the order of the *Thysanura*, for example *Lepisma saccharina;* from the order of the *Collembola*, for example *Onychiurus armatus;* from the order of the *Orthoptera*, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the *Dermaptera*, for example *Forficula auricularia;* from the order of the *Isoptera*, for example Reticulitermes spp.;

from the order of the *Anoplura*, for example *Phylloxera vastatrix*, Pemphigus spp., *Pediculus humanus corporis*, Haematopinus spp. and Linognathus spp.;

from the order of the *Mallophaga*, for example Trichodectes spp. and Damalinea spp.;

from the order of the *Thysanoptera*, for example *Hercinothrips femoralis* and *Thrips tabaci;* from the order of the *Heteroptera*, for example Eurygaster spp., *Dysdercus intermedius, Piesma quadrata, Cimex lectularius, Rhodnius prolixus* and Triatoma spp.;

from the order of the *Homoptera*, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma langigerum, Hyalopterus arundinis,* Macrospiphum avenae, Myzus spp., *Phorodon humuli, Rhopalosiphum padi,* Empoasca spp., *Euscelis bilobatus, Nephotettix cinciticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the *Lepidoptera,* for example [Pectinophora gossypiella, Bupalus piniarius, Chemimatobia brumata, Lithocolletis blancardella, Hypotomeuta padella, *Plutella maculipennis, Malacosoma neustria, Euproctis chrysorrhoae,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea,* Prodenia litura, Spodoptera spp., *Trichoplusia ni, Carpocapsa pomella,* Pieris spp., Chilo spp., *Pyrausta nubilalis, Ephestia kuehniella, Galleria mellonella, Cacoecia podana, Capua reticulana, Choristoneurea fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Onithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The active compounds are also suitable for combating pests in the veterinary field. In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from ectoparasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from ectoparasitical insects or acarids by the application to said animals of a compound according to the present invention, in admixture with a diluent or carrier.

The preparation of the novel compounds is shown in the following illustrative examples:

EXAMPLE 1

(a) The phenoxybenzyl bromides or phenoxybenzyl alcohols required as starting compounds could be prepared as follows:

48.4 g (0.22 mol) of 3-(3-fluorophenoxy)-6-fluorotoluene were dissolved in 300 ml of anhydrous carbon tetrachloride and heated under reflux with 41 g of N-bromosuccinimide. After 70° C. was reached, 3 g of azo-diisobutyronitrile were added; after about 10–20 minutes the reaction commenced, with evolution of heat, and after the exothermic reaction had subsided the mixture was heated under reflux for a further 4 hours. The reaction batch was then cooled to 10° C., the succinimide was filtered off and the carbon tetrachloride was distilled off in vacuo. The oil which remained was distilled at 142°–150° C./2 mm Hg. 3-(3-Fluorophenoxy)-6-fluorobenzyl bromide was obtained in 51% yield.

The following were prepared analogously:

TABLE 1

| Structure | Boiling point / Yield |
|---|---|
| F-phenyl-O-phenyl(F)-CH₂Br | Boiling point 140°–150° C./1 mm Hg, Yield: 45% of theory |
| F-phenyl-O-phenyl(F)-CH₂Br | Boiling point 142°–151° C./2 mm Hg, Yield: 47% of theory |
| (b) F-phenyl-O-phenyl(F)-CHO | |

56 g (0.187 mol) of 3-(4-fluorophenoxy)-4-fluoro-benzyl bromide and 53 g of hexamethylenetetramine in 500 ml of petroleum ether were heated under reflux for 3 hours, the mixture was then cooled to 5°–10° C., and the precipitate formed was filtered off. It was washed with 100 ml of petroleum ether, sucked dry and then heated, in 100 ml of 50% strength aqueous acetic acid, for 5 hours under reflux. 25 ml of concentrated hydrochloric acid were then added and the mixture was again heated under reflux for 30 minutes and then cooled to 10°–20° C. 200 ml of water were added to the reaction mixture, the batch was extracted twice with 150 ml of ether and the combined ether phases were then washed with sodium bicarbonate solution and dried over sodium sulphate. The ether was distilled off in vacuo. 3-(4-Fluorophenoxy)-4-fluoro-benzaldehyde, of boiling point 133°–135° C./1 mm Hg, was obtained in 40% yield.

The following was prepared analogously:

F-phenyl-O-phenyl(F)-CHO  Boiling point 138°–139° C./2 mm Hg, Yield: 46% of theory

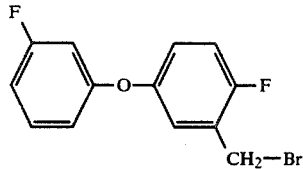

(c₁) F-phenyl-O-phenyl(F)-CH—OH
                                    |
                                    CN 9.6 g (0.041 mol) of 3-(4-fluorophenoxy)-4-fluorobenzaldehyde were dissolved in 50 ml of glacial acetic acid and 9 g of sodium cyanide, dissolved in 50 ml of water, were added dropwise at 15° C., while stirring. The reaction mixture was then stirred for 8 hours at 20° C., poured into 100 ml of water and extracted with 200 ml of ether, and the ether phase was washed with dilute sodium bicarbonate solution and was then dried over sodium sulphate. After distilling off the ether in vacuo, 3-(4-fluorophenoxy)-4-fluoro-α-cyanobenzyl alcohol having a refractive index $n_D^{24}$ of 1.5643 was obtained in 90% yield.

The following was prepared analogously:

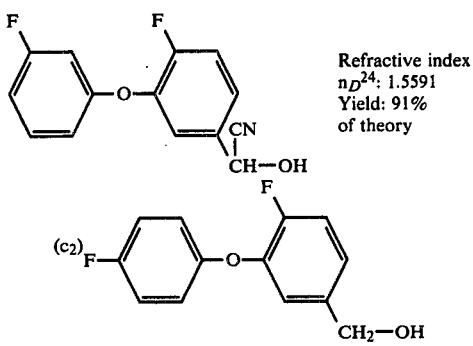

Refractive index $n_D^{24}$: 1.5591
Yield: 91% of theory 58.5 g (0.25 mol) of 3-(4-fluorophenoxy)-4-fluorobenzaldehyde, dissolved in 50 ml of dry ether, were added dropwise, with good stirring, to 3.8 g of lithium aluminum hydride in 100 ml of anhydrous ether. The reaction batch was then stirred for a further 10 hours at 22° C. and was cooled to 0° C., and ice-water was added dropwise, while stirring, until no further evolution of hydrogen was observed. The precipitate formed was dissolved by adding 10% strength sulphuric acid and the reaction mixture was then extracted twice with 100 ml of ether. The ether phases were separated off, washed with saturated sodium chloride solution and dried over sodium sulphate. After distilling off the ether in vacuo, 3-(4-fluorophenoxy)-4-fluorobenzyl alcohol of boiling point 155°–160° C./2 mm Hg was obtained in 80% yield.

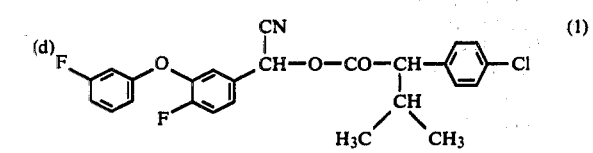

6.5 g (0.025 mol) of 3-(3-fluorophenoxy)-4-fluoro-α-cyanobenzyl alcohol and 5.8 g (0.025 mol) of α-isopropyl-4-chlorophenylacetic acid chloride were dissolved in 150 ml of anhydrous toluene and 2.4 g (0.03 mol) of pyridine, dissolved in 50 ml of toluene, were added dropwise at 25°–30° C., while stirring. The reaction mixture was then stirred for a further 3 hours at 25° C. and was poured into 150 ml of water, and the organic phase was separated off and washed with 100 ml of water. The toluene phase was then dried over sodium sulphate and the solvent was distilled off in a water-pump vacuum. The last remnants of solvent were removed by brief incipient distillation at 70° C. (bath temperature)/1 mm Hg. 7.5 g (65.9% of theory) of 3-(3-fluorophenoxy)-4-fluoro-α-cyanobenzyl α′-isopropyl-4′-chlorophenyl-acetate were obtained as a yellow oil having a refractive index $n_D^{25}$ of 1.5418.

EXAMPLE 2

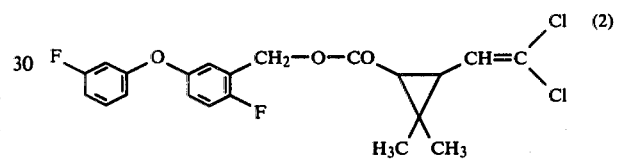

6.9 g (0.03 mol) of sodium 2,2-dimethyl-3-(2,2-dichlorovinyl)-cyclopropanecarboxylate were dissolved in 150 ml of dimethylformamide and heated, with 8.0 g (0.027 mol) of 3-(3-fluorophenoxy)-6-fluorobenzyl bromide, for 4 hours at 120° C. After completion of the reaction, the dimethylformamide was distilled off in vacuo and the residue was taken up in 200 ml of methylene chloride. This solution was then extracted by shaking twice with 150 ml of water, the organic phase was dried over sodium sulphate and the solvent was stripped off in vacuo. The last remnants of solvent were removed by brief incipient distillation at 70° C. (bath temperature)/1 mm Hg. 8.0 g (71% of theory) of 3-(3-fluorophenoxy)-6-fluorobenzyl 2,2-dimethyl-3-(2,2-dichlorovinyl)-cyclopropanecarboxylate were obtained as a yellow oil having a refractive index $n_D^{24}$ of 1.5395.

The following compounds could be prepared analogously:

TABLE 2

| Compound | Formula |
|---|---|
| 3 | ![structure] |

Refractive index $n_D^{26}$: 1.5326

TABLE 2-continued

| Compound | Formula |
|---|---|
| 4 | 3-(4-Fluorophenoxy)-4-fluoro-α-cyanobenzyl 3-(2,2-dichlorovinyl)-2,2-dimethylcyclopropanecarboxylate<br>Refractive index $n_D^{25}$: 1.5375 |
| 5 | 3-(3-Fluorophenoxy)-5-fluoro-α-cyanobenzyl 3-(2,2-dichlorovinyl)-2,2-dimethylcyclopropanecarboxylate |
| 6 | 4-(4-Fluorophenoxy)-3-fluorobenzyl 3-(2,2-dichlorovinyl)-2,2-dimethylcyclopropanecarboxylate |
| 7 | 3-(4-Fluorophenoxy)-4-fluoro-α-cyanobenzyl 3-(2,2-dibromovinyl)-2,2-dimethylcyclopropanecarboxylate |
| 8 | 3-(4-Fluorophenoxy)-4-fluoro-α-cyanobenzyl 2-(4-chlorophenyl)-3-methylbutyrate |
| 9 | 3-(4-Fluorophenoxy)-4-fluoro-α-cyanobenzyl 3-(2-methylpropenyl)-2,2-dimethylcyclopropanecarboxylate |
| 10 | 3-(3-Fluorophenoxy)-4-fluorobenzyl 3-(2,2-dichlorovinyl)-2,2-dimethylcyclopropanecarboxylate |
| 11 | 3-(3-Fluorophenoxy)-4-fluoro-α-cyanobenzyl 3-(2,2-dibromovinyl)-2,2-dimethylcyclopropanecarboxylate |
| 12 | 3-(3-Fluorophenoxy)-4-fluorobenzyl 3-(2,2-dibromovinyl)-2,2-dimethylcyclopropanecarboxylate |

*Note: The formulas shown are chemical structure diagrams. Names above are interpretive descriptions of the structures depicted.*

TABLE 2-continued

| Compound | Formula |
|---|---|
| 13 | 2-fluorophenoxy-phenyl-CH(CN)-O-CO-cyclopropyl(CH3)2-CH=CCl2 (with additional F on middle ring) |
| 14 | 4-fluorophenoxy-(3-fluoro)phenyl-CH(CN)-O-CO-cyclopropyl(CH3)2-CH=CCl2 |

The insecticidal and acaricidal activity of the compounds of this invention is illustrated by the following examples wherein the compounds according to the present invention are each identified by the number (given in brackets) from the preparative examples hereinabove:

EXAMPLE 3

Myzus test (contact action)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined and compounds (1), (3) and (4) showed a good action.

EXAMPLE 4

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined and compounds (1), (3) and (4) showed a good action.

EXAMPLE 5

Test insect: Tenebrio molitor larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined. Compound (3) showed a good action.

EXAMPLE 6

Test with parasitic fly larvae

Emulsifier: 80 parts by weight of alkylaryl glycol ether

To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction was determined.

In this test, compounds (3) and (4) showed a good action.

EXAMPLE 7

Test with parasitic adult cattle ticks
Solvent: Alkylaryl polyglycol ether

To produce a suitable preparation of active compound, the active substance in question was mixed with the stated solvent in the ratio of 1:2 and the concentrate thus obtained was diluted with water to the desired concentration.

10 adult cattle ticks (*Boophilus microplus* res.) were dipped for 1 minute into the active compound preparation to be tested. After transfer into plastic beakers and storage in a climatically controlled chamber, the degree of destruction in percent was determined.

In this test, compounds (3) and (4) showed a good action.

EXAMPLE 8

Test insects *Sitophilus granarius*
Solvent:   Acetone

The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test animals was observed 3 days after the commencement of the experiments.

In this test, compounds (1), (3) and (4) showed a good action.

It will be appreciated that the instant specification and examples are set forth by way of illustration and not limitation, and that various modifications and changes may be made without departing from the spirit and scope of the present invention.

What is claimed is:

1. A fluorine-substituted phenoxybenzylcarbonyl derivative of the formula

in which
R$^1$ represents hydrogen, cyano or ethynyl and
R$^2$ represents the radical

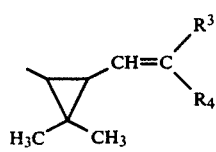

wherein
R$^3$ and R$^4$, which are identical, each represent chlorine, bromine or methyl, or
R$^2$ represents the radical

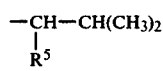

wherein
R$^5$ represents a phenyl ring which optionally carries one or more substituents each selected independently from halogen, alkyl, alkylthio and alkoxy each with 1-4 carbon atoms, nitro and methylenedioxy.

2. A compound according to claim 1, in which R$^1$ represents hydrogen or cyano and R$^2$ represents the 2,2-dimethyl-3-(2,2-dichloro- 2,2-dibromo- or 2,2-dimethyl-vinyl)-cyclopropane radical or the α-isopropylbenzyl) radical which optionally carries one or more substituents in the ring selected independently from fluorine, chlorine, bromine and straight-chain or branched alkyl with 1 to 3 carbon atoms.

3. A compound according to claim 1, wherein such compound is 3-(3-fluorophenoxy)-4-fluoro-α-cyanobenzyl α$^1$-isopropyl-4'-chlorophenyl-acetate of the formula

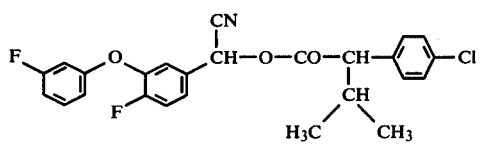

4. A compound according to claim 1, wherein such compound is 3-(3-fluorophenoxy)-6-fluorobenzyl 2,2-dimethyl-3-(2,2-dichlorovinyl)-cyclopropanecarboxylate of the formula

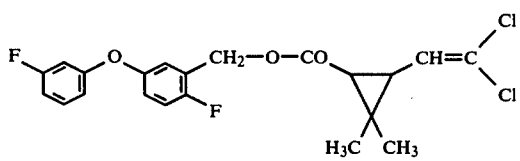

5. A compound according to claim 1, wherein such compound is 3-(4-fluorophenoxy)-4-fluoro-α-cyanobenzyl 2,2-dimethyl-3-(2,2-dichlorovinyl)-cyclopropanecarboxylate of the formula

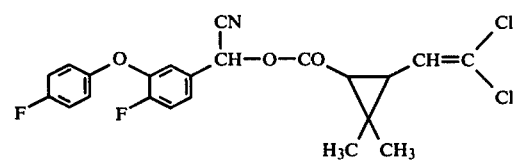

6. A compound according to claim 1, wherein such compound is 3-(3-fluorophenoxy)-4-fluoro-α-cyanobenzyl 2,2-dimethyl-3-(2,2-dichlorovinyl)-cyclopropanecarboxylate of the formula

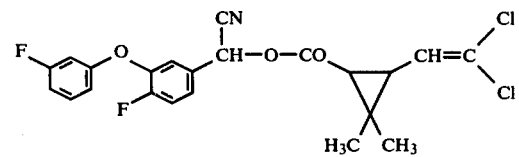

7. An arthropodicidal composition containing as active ingredient an arthropodicidally effective amount of a compound according to claim 1 in admixture with a diluent.

8. A method of combating arthropods which comprises applying to the arthropods, or to a habitat thereof, an arthropodicidally effective amount of a compound according to claim 1.

9. The method according to claim 8, in which said compound is
- 3-(3-fluorophenoxy)-4-fluoro-α-cyanobenzyl $^1$-isopropyl-4'-chlorophenyl-acetate,
- 3-(3-fluorophenoxy)-6-fluorobenzyl 2,2-dimethyl-3-(2,2-dichlorovinyl)-cyclopropanecarboxylate or
- 3-(4-fluorophenoxy)-4-fluoro-α-cyanobenzyl 2,2-dimethyl-3-(2,2-dichlorovinyl)-cyclopropanecarboxylate, and is applied to domesticated animals thereby to free such animals from ectoparasitical insects and acarids.

* * * * *